(12) United States Patent
Guglielmotti et al.

(10) Patent No.: US 7,638,534 B2
(45) Date of Patent: Dec. 29, 2009

(54) USE OF INDAZOLE DERIVATIVES FOR THE TREATMENT OF NEUROPATHIC PAIN

(75) Inventors: Angelo Guglielmotti, Rome (IT); Lorenzo Polenzani, Grottaferrata (IT); Alessandra Alisi, Rome (IT); Nicola Cazzolla, Albano Laziale (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 576 days.

(21) Appl. No.: 10/564,854

(22) PCT Filed: Jul. 8, 2004

(86) PCT No.: PCT/EP2004/007635

§ 371 (c)(1),
(2), (4) Date: Jan. 17, 2006

(87) PCT Pub. No.: WO2005/013989

PCT Pub. Date: Feb. 17, 2005

(65) Prior Publication Data

US 2006/0183775 A1 Aug. 17, 2006

(30) Foreign Application Priority Data

Jul. 18, 2003 (IT) .......................... MI2003A1468

(51) Int. Cl.
*A61K 31/445* (2006.01)
*A01N 43/40* (2006.01)

(52) U.S. Cl. ..................... 514/318; 514/321; 514/322

(58) Field of Classification Search .............. 514/318, 514/321, 322
See application file for complete search history.

(56) References Cited

U.S. PATENT DOCUMENTS

| 5,817,676 | A | 10/1998 | Catlow et al. | |
| 6,624,162 | B2 * | 9/2003 | Uchida et al. | 514/233.2 |
| 2006/0052417 | A1 | 3/2006 | Alisi et al. | |

FOREIGN PATENT DOCUMENTS

| EP | 0 884 319 | 12/1998 |
| EP | 0 630 376 | 6/1999 |
| EP | 0 975 623 | 2/2000 |
| WO | 93/03725 | 3/1993 |
| WO | 93/06108 | 4/1993 |
| WO | 2004/014922 | 2/2004 |

OTHER PUBLICATIONS

Pain and Nociception, Wikipedia, p. 1-7.*
Pain and Nociception, Wikipedia, p. 1-7, 2007.*
Doak, G.J.; Sawynok, J.: "Formalin-Induced Nociceptive Behavior and Edema: Invovlement of Multiple Peripheral 5-Hydroxytryptamine Receptor Subtypes" Neurosience, vol. 80, No. 3, 1997, pp. 939-949, XP002279566.

Donahue, et al.; "Electrolytic Lesion of the Anterior Cingulate Cortex Decreases Inflammatory, but not Neuropathic Nociceptive Behavior in Rats" Brain Research, vol. 897, No. 1-2, 2001, pp. 131-138, XP002279567.

Beers, M. and Berkow, R.: "The Merck Manual of Diagnosis and Therapy, Seventeenth Edition" 1999, Merck Research Laboratories, Whitehouse Station, N.J., XP002279568, p. 1371-1372.

Espejoe, et al.: "Antagonism of Peripheral 5-HT4 Receptors Reduces Visceral and Cutaneous Pain in Mice, and Induces Visceral Analgsia After Simultaneous Inactivation f 5-HT3 Receptors" Brain Research, Amsterdam, NL; vol. 788, No. 1/2, 1998, pp. 20-24 XP001064161.

Torssell, Kurt et al., "Isolation, Structure and Synthesis of Alkaloids From Valeriana Officinalis L", Acta Chemica Scandinavica 21 (1), pp. 53-62, 1967.

Ashburn, Michael A., Staats, Peter S.: "Management of Chronic Pain", The Lancet, vol. 353, pp. 1865-1869, 1999.

Bannon, A.W., et al.: "ABT-594, a novel cholinergic channel modulator is efficacious in nerve ligation and diabetic neuropathy models of neuropathic pain" Brain Research, vol. 801, pp. 158-163, 1998.

Bennett, Gary J. and Xie, Y.K.: "A Peripheral Mononeuropathy in Rat that Produces Disorders of Pain Sensation Like Those Seen in Man", Pain, 33, pp. 87-107, 1988.

Courteix, C., Eschalier, A., and Lavarenne, J.: "Streptozocin-Induced Diabetic Rats: Behavioural Evidence for a Model of Chronic Pain", Pain, 53, pp. 81-88, 1993.

(Continued)

*Primary Examiner*—Sreeni Padmanabhan
*Assistant Examiner*—Umamaheswari Ramachandran
(74) *Attorney, Agent, or Firm*—Oblon, Spivak, McClelland, Maier & Neustadt, L.L.P.

(57) ABSTRACT

Use of a compound of formula (I), wherein X is CH or N, and when X is CH, R is H, OH, a linear or branched alkyl chain having from 1 to 3 carbon atoms, a linear or branched alkoxy chain having from 1 to 3 carbon atoms, or a halogen atom, and when X is N, R is H, or an acid addition salt thereof with a pharmaceutically acceptable organic or inorganic acid, to prepare a pharmaceutical composition active in the treatment of neuropathic pain.

(I)

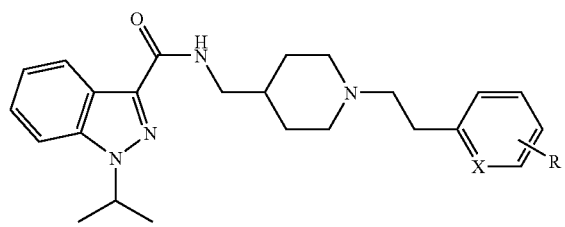

15 Claims, 1 Drawing Sheet

OTHER PUBLICATIONS

Scholz, J. and Woolf, C.J.: "Can We Conquer Pain?", Nature Neuroscience, vol. 5, pp. 1062-1067, Nov. 2002.
Seltzer, Z. et al.: "A Novel Behavioral Model of Neuropathic Pain Disorders Produced in Rats by Partial Sciatic Nerve Injury", Pain, 43, pp. 205-218, 1990.
Woolf, CLifford J. et al.: "Neuropathic Pain: Aetiology, Symptoms, Mechanisms, and Management", The Lancet, vol. 353, pp. 1959-1964, Jun. 5, 1999.
U.S. Appl. No. 10/549,930, filed Sep. 20, 2005, Alisi, et al.
U.S. Appl. No. 10/560,836, filed Dec. 15, 2005, Guglielmotti, et al.
Houghton et al. "5-$HT_4$ receptor antagonism in irritable bowel syndrome: effect of SB-207266-A on rectal sensitivity and small bowel transit", Aliment Pharmacol Ther, vol. 13, pp. 1437-1444, 1999.
Wei et al. "Influence of Two Serotonin Receptor Antagonists in Neuropathic Rats", Pfluegers Archiv European Journal of Physiology, vol. 443, No. supplement 1, p. S181, 2002.
Smith, M.I., et al., "5-$HT_4$ receptor antagonism potentiates inhibition of intestinal allodynia by 5-$HT_3$ receptor antagonism in conscious rats" Neuroscience Letters 271 (1999), pp. 61-64.
Jorum E., et al., "Cold allodynia and hyperalgesia in neuropathic pain: the effect of N-methyl-D-aspartate (NMDA) receptor antagonist ketamine—a double-blind, cross-over comparison with alfentanil and placebo", Pain 101 (2003) pp. 229-235.
Burstein R., et al., "The development of cutaneous allodynia during a migraine attack—Clinical evidence for the sequential recruitment of spinal and supraspinal nociceptive neurons in migraine", Brain (2000), 123, pp. 1703-1709.
Neuropathic pain causes, symptoms, diagnosis, and treatments on MedicineNet.com, Pain Management: Neuropathic Pain (3 pages), 2008.
Dorlands Medical Dictionary, Dorland's Illustrated Medical Dictionary (22 pages), 2008.
Abdominal Pain Causes, Symptoms, Diagnosis and Treatment by MedicineNet.com, Abdominal Pain Index (3 pages), 2008.
Allodynia—Wikipedia, the free encyclopedia, Allodynia (5 pages), 2008.
Pain and nociception—Wikipedia, the free encyclopedia, Pain and nociception (7 pages), 2007.
Hyperalgesia—Wikipedia, the free encyclopedia, Hyperalgesia (1 page), 2007.
Migraine—Wikipedia, the free encyclopedia, Migraine (8 pages), 2007.
Medical Hypotheses -Elsevier, Guide for Authors (4 pages), 2008.
Omoigui S., The biochemical origin of pain—Proposing a new law of pain: The origin of all pain is imflammation and the inflammatory response. Part 1 of 3—A unifying law of pain, Medical Hypotheses, vol. 69, Issue 1 (13 pages), 2006.
Omoigui S., "The biochemical origin of pain: The origin of all pain is inflammation and the inflammatory response. Part 2 of 3—Inflammatory profile of pain syndromes". Medical Hypotheses (13 pages), 2007.
Hill R., "$NK_1$ (substance P) receptor antagonists—why are they not analgesic in humans?", Viewpoint, Trends in Pharmacological Sciences, Jul. 2000, vol. 21 (3 pages).
Ahmed M., et al. "Management Strategies for the Treatment of Neuropathic Pain in the Elderly", Drugs Aging, 2002:19(12), pp. 929-945.
Sadosky, A., et al., "A Review of the Epidemiology of Painful Diabetic Peripheral Neuropathy, Postherpetic Neuralgia, and Less Commonly Studied Neuropathic Pain Conditions", Pain Practice, vol. 8, Issue 1, 2008 pp. 45-56.
Do, Katheirne E. Galluzzi, "Managing Neuropathic Pain", JAOA, Supplemental 6, vol. 107. No. 11, Nov. 2007.
Paice, J. A., "Mechanisms and Management of Neuropathic Pain in Cancer", The Journal of Supportive Oncology, vol. 1, No. 2, Jul./Aug. 2003 pp. 107-120.
Veves, A., et al., "Painful Diabetic Neuropathy: Epidemiology, Natural History, Early Diagnosis, and Treatment Options", Pain Medicine, vol. 9, No. 6, 2008, pp. 660-674.
Verma, S., et al., "HIV-Associated Neuropathic Pain, Epidemiology, Pathophysiology and Management", CNS Drugs, 2005, 19 (4), pp. 325-334.
Tremont-Lukats,I.W., et al., "Anticonvulsants for Neuropathic Pain Syndromes—Mechanisms of Action and Place in Therapy", Drugs, Nov. 2000, 60 (5), pp. 1029-1052.
Gray P., "Acute neuropathic pain: diagnosis and treatment", Current Opinion in Anaesthesiology, 2008, 21, pp. 590-595.
Finnerup, N. B, "A review of central neuropathic pain states", Current Opinion in Anaesthesiology, 2008, 21, pp. 586-589.

* cited by examiner

TABLE 1
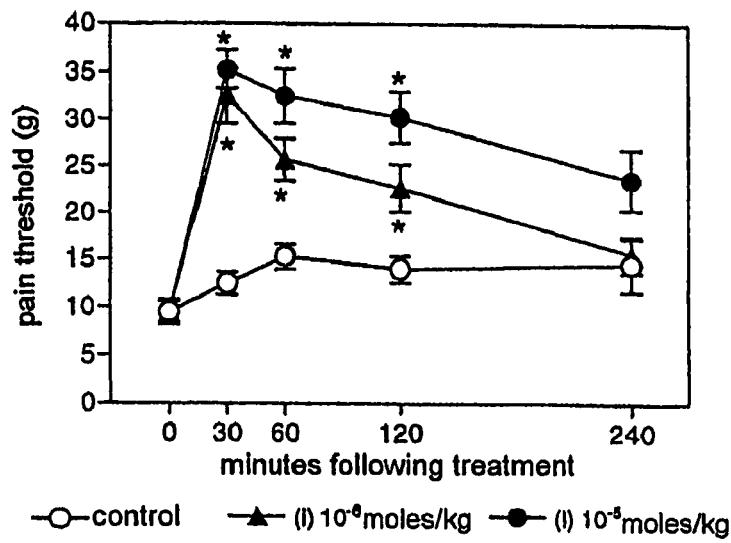
Fig. 1 Effect on sciatic nerve ligature
8 rats/group; mean ± SEM; *p < 0.05 vs. control, ANOVA followed by Dunnett's test
Pain threshold of normal animals of equal weight/age = 35.4 ± 3.22 g
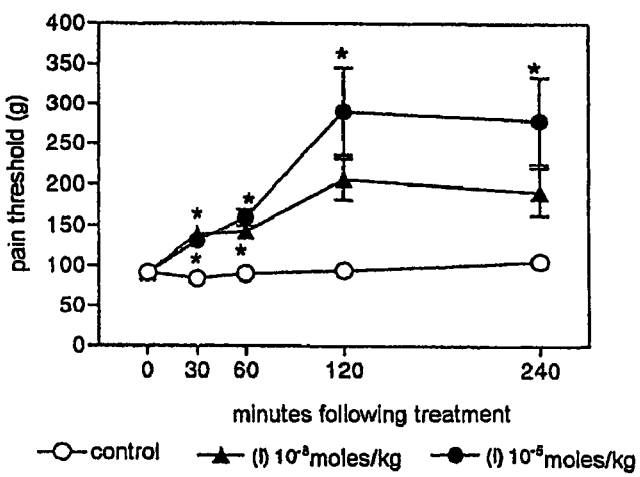
Fig. 2 Effect on diabetic neuropathy
8 rats/group; mean ± SEM; *p < 0.05 vs. control, ANOVA followed by Dunnett's test
Pain threshold of normal animals of equal weight/age = 252.5 ± 6.20 g

USE OF INDAZOLE DERIVATIVES FOR THE TREATMENT OF NEUROPATHIC PAIN

The present invention relates to the use of an indazole compound for the preparation of a pharmaceutical composition active in the treatment of neuropathic pain.

Patent applications EP-A-0 975 623 and WO 93/03725 relate to a large number of compounds of formula I:

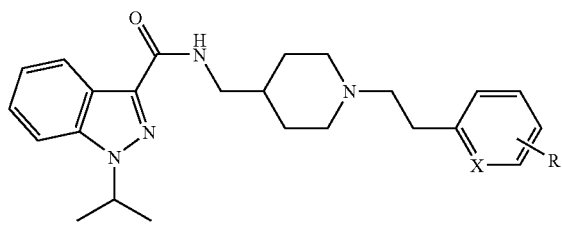

(I)

including those wherein

X is CH or N, and when X is CH, R is H, OH, a linear or branched alkyl chain having from 1 to 3 carbon atoms, a linear or branched alkoxy chain having from 1 to 3 carbon atoms, or a halogen atom, and when X is N, R is H.

Hereinafter, the compounds of formula (I) wherein R and X have the aforesaid meanings will for brevity be referred to as "Compound (I)".

According to the aforesaid documents, Compound (I) is active in the treatment of disorders of gastrointestinal motility, urinary incontinence, cardiac arrhythmia and disorders of the central nervous system such as memory disorders and anxiety.

It has now surprisingly been found that Compound (I) is particularly active in neuropathic pain.

It is known that on average about 10-20% of the adult population suffer from chronic pain. The chronic pain is generally associated with clinical conditions characterised by chronic and/or degenerative lesions.

Typical examples of pathological conditions characterised by chronic pain are rheumatoid arthritis, osteoarthritis, fibromyalgia, neuropathy, and the like [Ashburn M A, Staats P S, Management of chronic pain. Lancet 1999; 353: 1865-69].

Chronic pain, in particular neuropathic pain, is often debilitating and is a cause of loss of working capacity and poor quality of life. Consequently, it also results in economic and social losses.

The analgesic drugs currently used in the treatment of neuropathic pain include non-steroidal anti-inflammatories (NSAIDs), antidepressants, opioid analgesics, and anticonvulsants [Woolf C J, Mannion R J. Neuropathic pain: aetiology, symptoms, mechanism, and management. Lancet 1999; 353: 1959-1964].

However, chronic pain and, in particular, neuropathic pain is notoriously difficult to treat with the drugs currently available. Consequently, the development of novel analgesics has always been one of the major targets of the pharmaceutical industry. Moreover, in spite of the many research efforts intended to identify a suitable analgesic compound, there are a significant number of patients for whose pain condition there is still no satisfactory treatment [Scholz J, Woolf C J. Can we conquer pain? Nat Neusci. 2002; 5: 1062-76].

The present invention thus relates to the use of a compound of formula (I):

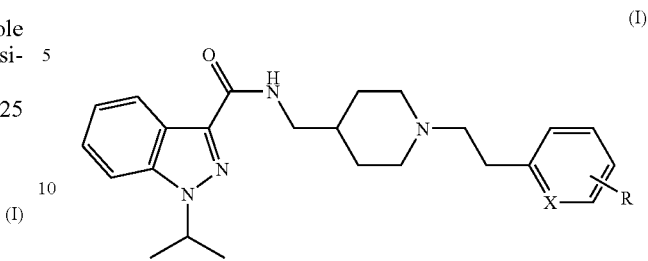

(I)

wherein

X is CH or N, and when X is CH, R is H, OH, a linear or branched alkyl chain having from 1 to 3 carbon atoms, a linear or branched alkoxy chain having from 1 to 3 carbon atoms, or a halogen atom, and when X is N, R is H, or of an acid addition salt thereof with a pharmaceutically acceptable organic or inorganic acid, to prepare a pharmaceutical composition active in the treatment of neuropathic pain.

Typical examples of pharmaceutically acceptable organic and inorganic acids are: oxalic, maleic, methanesulphonic, paratoluenesulphonic, succinic, citric, tartaric, lactic, hydrochloric, phosphoric and sulphuric.

Typical examples of pathological conditions characterised by neuropathic pain are diabetes, cancer, immunodeficiency, traumas, ischaemia, multiple sclerosis, sciatic neuralgia, trigeminal neuralgia and post-herpetic syndromes.

Preferably, the pharmaceutical compositions of the present invention are prepared in the form of suitable dosage forms containing an effective dose of at least one Compound (I) or of an acid addition salt thereof with a pharmaceutically acceptable organic or inorganic acid and at least one pharmaceutically acceptable inert ingredient.

Examples of suitable dosage forms are tablets, capsules, coated tablets, granules, solutions and syrups for oral administration; medicated plasters, solutions, pastes, creams and ointments for transdermal administration; suppositories for rectal administration and sterile solutions for administration by the injection or aerosol routes.

Other suitable dosage forms are the sustained release dosage forms or the dosage forms based on liposomes for oral or injection administration.

The dosage forms may also comprise other conventional ingredients such as: preservatives, stabilisers, surfactants, buffers, salts to regulate the osmotic pressure, emulsifiers, sweeteners, colorants, flavourings and the like.

If required by particular therapies, the pharmaceutical composition of the present invention may comprise other pharmacologically active ingredients whose concomitant administration is useful.

The amount of Compound (I) or of an acid addition salt thereof with a pharmaceutically acceptable acid in the pharmaceutical composition of the present invention can vary over a wide range depending on known factors such as, for example, the type of pathology with which the neuropathic pain to be treated is associated, the severity of the disease, the patient's body weight, the dosage form, the chosen administration route, the number of administrations per day and the efficacy of the chosen compound of formula (I). However, the optimal amount can be determined in a simple and routine manner by the person skilled in the art.

Typically, the amount of Compound (I) or of an acid addition salt thereof with a pharmaceutically acceptable acid in the pharmaceutical composition of the present invention will be such as to ensure an administration level of from 0.001 to 100 mg/kg/day of Compound (I), as a base. Preferably, the administration level will be of from 0.05 to 50 mg/kg/day, and still more preferably of from 0.1 to 10 mg/kg/day.

The dosage forms of the pharmaceutical composition of the present invention can be prepared by techniques well known to the pharmaceutical chemist which include mixing, granulating, compressing, dissolving, sterilizing and the like.

The analgesic activity of Compound (I) has been proved by means of two experimental models in the rat: allodynia induced by ligature of the sciatic nerve and mechanical hyperalgesia in diabetic neuropathy induced by streptozotocin.

As is known to the person skilled in the art, the aforesaid experimental models can be considered to be predictive of activity in man.

The experimental model of ligature of the sciatic nerve in the rat is a neuropathy which reproduces a series of responses similar to those observed in man in many traumatic and pathological conditions associated with neuropathic pain. Ligature of the sciatic nerve is in fact capable of inducing a syndrome associated with the activation of specific circuits responsible for the control of the perception of pain and characterised by the appearance of allodynia, hyperalgesia and spontaneous pain. As is well known, this model is an effective instrument for the study of drugs for use in the treatment of neuropathic pain in man and, in particular, in the control of conditions such as allodynia and hyperalgesia.

In its turn, the diabetic neuropathy induced by streptozotocin in the rat is an insulin-dependent syndrome characterised by a concomitant decrease in the conduction speed of the motor and sensory nerves and the appearance of a series of anomalies in the perception of pain. As is well known, this model is a useful instrument for the study of drugs for use in the treatment of neuropathic pain in man. In particular, the model is a valid example of a large group of neuropathic pain types characterised by phenomena such as hyperalgesia and allodynia due to primary lesions or dysfunctions of the nervous system.

Typical examples of human pathologies characterised by the dysfunctions described in the two experimental models cited above and characterised by the presence of neuropathic pain are diabetes, cancer, immunodeficiency, trauma, ischaemia, multiple sclerosis, sciatic neuralgia, trigeminal neuralgia and post-herpetic syndromes.

BRIEF DESCRIPTION OF THE DRAWINGS

FIG. 1. Effect on sciatic nerve ligature. The pain thresholds of rats treated with compound (I) and control rats were compared. 8 rats/group, mean ±SEM; *$p<0.05$ vs. control, ANOVA followed by Dunnett's test. Pain threshold of normal animals of equal weight/age=35.4±3.22 g.

FIG. 2. Effect on diabetic neuropathy. The pain thresholds of rats treated with compound (I) and control rats were compared. 8 rats/group, mean ±SEM; *$p<0.05$ vs. control, ANOVA followed by Dunnett's test. Pain threshold of normal animals of equal weight/age=252.5±6.20 g.

TESTS

1. Allodynia Induced by Ligature of the Sciatic Nerve in the Rat

Male CD rates of weight 200-250 g on arrival were used.

The allodynia was induced by ligature under anaesthesia of the sciatic nerve of the left hind paw [Seltzer Z, Dubner R, Shir Y. A novel behavioral model of neuropathic pain disorders produced in rats by partial sciatic nerve injury. Pain 1990; 43: 205-218; Bennett G J, Xie Y K. A peripheral mononeuropathy in rat that produces disorders of pain sensation like those seen in man. Pain 1998; 33: 87-107]. After at least two weeks following the ligature of the sciatic nerve, rats which showed a reduction of a least 50% in the response threshold recorded before the operation were selected. The pain threshold was measured by means of a von Frey instrument which, by applying a gradual increase in pressure on the plantar zone of the left hind paw of the rat, makes it possible to record the nocifensive response, expressed in grams, corresponding to the moment at which the animal withdraws its paw.

At 30 minutes, 1, 2 and 4 hrs after the treatment, the pain threshold measured in control animals was compared with that measured in animals treated with the hydrochloride salt of Compound (I) under test wherein R=4-OH and X=CH.

The control animals were treated with same vehicle (water) as was used for administration of the product under test. The results are shown in FIG. 1.

Similar results were obtained with the hydrochloride salts of Compounds (I) prepared according to Examples 2 (I, X=CH, R=H) and 10 (I, X=N, R=H) of EP-A-0 975 623.

2. Mechanical Hyperalgesia in Rats with Diabetes Induced by Streptozotocin

Male CD rates of weight 240-300 g on arrival were used.

The diabetic syndrome was induced by a single intraperitoneal (i.p.) injection of 80 mg/kg of streptozotocin dissolved in sterile physiological solution [Courteix C, Eschalier A, Lavarenne J. Streptozotocin-induced diabetic rats: behavioural evidence for a model of chronic pain. Pain, 1993; 53: 81-88; Bannon A W, Decker M W, Kim Dj, Campbell J E, Arneric S P. ABT-594, a novel cholinergic channel modulator, is efficacious in nerve ligation and diabetic neuropathy models of neuropathic pain. Brain Res. 1998; 801: 158-63].

After at least three weeks following the injection of streptozotocin, rats with a glycaemia level≧300 mg/dl and a response threshold≦120 g to a mechanical nociceptive stimulus were selected. The glycaemia levels were measured using a reflectometer utilising reactive strips impregnated with glucose oxidase. The pain threshold was measured using an analgesimeter. The instrument, by applying a gradual increase in pressure on the dorsal zone of the left hind paw of the rat, makes it possible to record the nocifensive response, expressed in grams, corresponding to the moment at which the animal withdraws its paw.

At 30 minutes, 1, 2 and 4 hrs after the treatment, the pain threshold measured in control animals was compared with that measured in animals treated with the hydrochloride salt of Compound (I) under test wherein R=4-OH and X=CH.

The control animals were treated with same vehicle (water) as was used for administration of the hydrochloride salt of Compound (I) under test.

The results are shown in FIG. 2.

Similar results were obtained with the hydrochloride salts of Compounds (I) prepared according to Examples 2 (I, X=CH, R=H) and 10 (I, X=N, R=H) of EP-A-0 975 623.

EXAMPLES

Example 1

N((1-(2-(4-hydroxyphenyl)ethyl)-4-piperidinyl)methyl)-1-isopropyl-1H-indazole-3-carboxamide hydrochloride (Compound I, R=OH, X=CH)

Method A)

a) N-hexahydro-4-piperidinylmethyl-N-phenylmethylideneamine

Benzaldehyde (38.2 g, 0.36 moles) was added dropwise to a solution of 4-aminomethyl-piperidine (41.1 g, 0.36 moles)

in toluene (180 ml). The solution thus obtained was left at room temperature with stirring for 3 hrs. The solvent was then removed by evaporation under reduced pressure and the residue was taken up twice with toluene to give the desired product which was used without further purification.

b) 1-(2-(4-hydroxyphenyl)ethyl)-4-piperidinylmethanamine

The product obtained in step 1a) (63.2 g, 0.31 moles) was dissolved in absolute ethanol (50 ml) and added to a suspension of 2-(4-hydroxyphenyl)ethyl bromide (prepared as described in Acta Chem. Scand. 21 (1) 53-62, 1967) (62.8 g, 0.31 moles), and anhydrous potassium carbonate (64.7 g, 0.47 moles) in 150 ml of absolute ethanol. The suspension thus obtained was boiled under reflux for 16 hours. The reaction mixture was then allowed to cool to ambient temperature and filtered. The filtrate was evaporated under reduced pressure. The residue thus obtained was suspended in 3N HCl (280 ml) and left at ambient temperature with stirring for 3 hours. The solution was then transferred into a separatory funnel and the acidic aqueous phase was washed with ethyl acetate (4×200 ml); the aqueous phase was then made alkaline to pH=12 by addition of 6N NaOH. The solid that was formed was separated by filtration and crystallised from absolute ethanol to give the desired product (35 g). m.p.=166-168° C.

$^1$H NMR (δ, DMSO+D$_2$O): 0.95-1.30 (m, 3H); 1.52-1.73 (m, 2H); 1.90 (t, J=11 Hz, 2H); 2.30-2.75 (m, 6H); 2.80-2.95 (m, 2H); 6.65 (d, J=9 Hz, 2H); 6.98 (d, J=9 Hz, 2H).

c) N((1-(2-(4-hydroxyphenyl)ethyl)-4-piperidinyl)methyl)-1-isopropyl-1H-indazole-3-carboxamide hydrochloride A solution of the product obtained in step 1b) (10.0 g, 0.043 moles) and triethyl-amine (30 ml, 0.21 moles) in DMF (100 ml) was added dropwise to a solution of 1-(1-methylethyl)-1H-indazole-3-carboxylic acid chloride (9.5 g, 0.043 moles), prepared as described in EP-A-0 975 623, in DMF (50 ml). After having been stirred continuously at room temperature for 18 hrs, the reaction mixture was transferred into a separatory funnel, added with H$_2$O, and extracted with ethyl acetate (3×150 ml). The organic phase was separated and dried over Na$_2$SO$_4$. The solvent was removed by evaporation under reduced pressure. The residue thus obtained was taken up with absolute ethanol and transformed into the corresponding hydrochloride salt by addition of ethanolic hydrogen chloride. The solution was evaporated under reduced pressure and the residue was crystallised from ethanol to give the desired product (20 g).

Method B)

2-(4-hydroxyphenyl)ethyl bromide (prepared as described in Acta Chem. Scand. 21 (1) 53-62, 1967) (3.4 g, 0.017 moles) and anhydrous potassium carbonate (4.6 g, 0.033 moles) in absolute ethanol (100 ml) were added to a solution of N-(4-piperidinylmethyl)-1-isopropyl-1H-3 indazolecarboxamide (4.2 g, 0.014 moles), prepared as described in EP-A-0 975 623 in absolute ethanol (80 ml). The suspension thus obtained was stirred continuously under reflux for 16 hours. The suspension was filtered and the filtrate evaporated under reduced pressure. The residue thus obtained was then transformed into the corresponding hydrochloride salt by dissolution in ethyl acetate, addition of ethanolic hydrogen chloride and recrystallisation from absolute ethanol to give the desired product (2.2 g).

m.p.=218-220° C.

| Elemental analysis C$_{25}$H$_{32}$N$_4$O$_2$HCl | C | H | N |
|---|---|---|---|
| % found | 65.66 | 7.26 | 12.14 |
| % calculated | 65.70 | 7.28 | 12.26 |

$^1$H NMR (DMSO, δ): 1.55 (d, J= 7 Hz, 6H); 1.63-2.15 (m, 5H); 2.70-3.75 (m, 10H); 5.09 (heptet, J= 7 Hz, 1H); 6.75 (d, J= 8 Hz, 2H); 7.06 (d, J= 8 Hz, 2H); 7.21-7.30 (m, 1H); 7.40-7.50 (m, 1H); 7.8 (d, J= 8 Hz, 1H); 8.21 (d, J= 8 Hz, 1H); 8.46 (m, 1H); 9.40 (s, 1H); 10.80 (s broad, 1H).

Example 2

A tablet comprising, as the active principle, a Compound (I) of the present invention, has the following composition:

| | |
|---|---|
| Active principle | 50 mg |
| Lactose monohydrate | 161 mg |
| Dibasic calcium phosphate dihydrate | 161 mg |
| Microcrystalline cellulose | 95 mg |
| Maize starch | 30 mg |
| Sodium carboxymethyl starch | 24 mg |
| Povidone | 11 mg |
| Magnesium stearate | 3 mg |

Example 3

An ampoule comprising, as the active principle, a Compound (I) of the present invention, has the following composition:

| | |
|---|---|
| Active principle | 25 mg |
| Sorbitol | q.s. for isosmotic solution |
| Water | q.s to 100 ml |

Example 4

A pharmaceutical composition in granules comprising, as the active principle, a Compound (I) of the present invention, has the following composition:

| | |
|---|---|
| Active principle | 50 mg |
| Maltitol | 1300 mg |
| Mannitol | 2700 mg |
| Saccharose | 1000 mg |
| Citric acid | 20 mg |
| Aspartame | 20 mg |
| Flavourings | 200 mg |

The invention claimed is:

1. A method for treating neuropathic pain comprising administering to a human subject having neuropathic pain, 0.001 to 100 mg/kg/day of to a subject having neuropathic pain the compound of formula I:

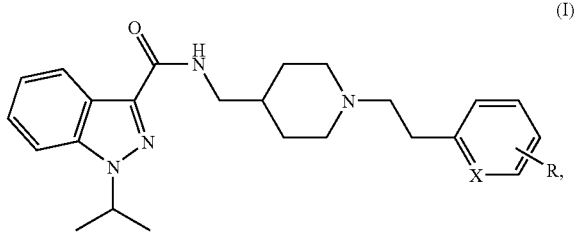

(I)

wherein X is CH or N, and
when X is CH, R is H, OH, a linear or branched alkyl chain having from 1 to 3 carbon atoms, a linear or branched alkoxy chain having from 1 to 3 carbon atoms, or a halogen atom, and
when X is N, R is H;
or an acid addition salt thereof with a pharmaceutically acceptable organic or inorganic acid.

2. The method of claim 1, wherein X is N and R is H in the compound of formula (I).

3. The method of claim 1, wherein X is CH and R is H in the compound of formula (I).

4. The method of claim 1, wherein X is CH and R is OH in the compound of formula (I).

5. The method of claim 1, wherein X is CH and R is halogen in the compound of formula (I).

6. The method of claim 1, wherein X is CH and R is a linear or branched alkyl chain having from 1 to 3 carbon atoms in the compound of formula (I).

7. The method of claim 1, wherein X is CH and R is a linear or branched alkoxy chain having from 1 to 3 carbon atoms in the compound of formula (I).

8. The method of claim 1, wherein the human has neuropathic pain resulting from diabetes.

9. The method of claim 1, wherein the human has neuropathic pain resulting from immunodeficiency.

10. The method of claim 1, wherein the human has neuropathic pain resulting from trauma.

11. The method of claim 1, wherein the human has neuropathic pain resulting from ischaemia.

12. The method of claim 1, wherein the human has neuropathic pain resulting from multiple sclerosis.

13. The method of claim 1, wherein the human has neuropathic pain resulting from sciatic neuralgia.

14. The method of claim 1, wherein the human has neuropathic pain resulting from trigeminal neuralgia.

15. The method of claim 1, wherein the human has neuropathic pain resulting from a post-herpetic syndrome.

* * * * *